(12) United States Patent
Terauchi et al.

(10) Patent No.: US 7,800,493 B2
(45) Date of Patent: *Sep. 21, 2010

(54) COMMUNICATION APPARATUS AND COMMUNICATION METHOD

(75) Inventors: Toshiro Terauchi, Tokyo (JP); Yoichiro Sako, Tokyo (JP); Akiko Inoue, Saitama (JP); Makoto Inoue, Kanagawa (JP); Katsuya Shirai, Kanagawa (JP); Yasushi Miyajima, Kanagawa (JP); Kenichi Makino, Kanagawa (JP); Motoyuki Takai, Tokyo (JP)

(73) Assignee: Sony Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/409,135

(22) Filed: Apr. 21, 2006

(65) Prior Publication Data

US 2006/0197657 A1    Sep. 7, 2006

Related U.S. Application Data

(63) Continuation of application No. 10/863,440, filed on Jun. 8, 2004, now Pat. No. 7,199,708.

(30) Foreign Application Priority Data

Jun. 30, 2003   (JP)   ............... 2003-188421

(51) Int. Cl.
    *G08B 1/08* (2006.01)
(52) U.S. Cl. ............... 340/539.12; 128/903; 600/300
(58) Field of Classification Search ............ 340/539.12, 340/539.22, 539.26, 539.29, 539.13, 573.1, 340/693.5, 693.9, 870.16, 5.82; 600/300, 600/549, 323, 9; 128/903, 898; 235/375, 235/492

See application file for complete search history.

(56) References Cited

U.S. PATENT DOCUMENTS 4,819,860 A    4/1989   Hargrove et al.

(Continued)

FOREIGN PATENT DOCUMENTS

CA    2446488    11/2002

(Continued)

OTHER PUBLICATIONS

Japanese Office Action issued Aug. 15, 2006 (Japanese language only).

*Primary Examiner*—Brent Swarthout
(74) *Attorney, Agent, or Firm*—Lerner, David, Littenberg, Krumholz & Mentlik, LLP

(57) ABSTRACT

By providing bio-information and/or environment information between a pair of users, it becomes possible for the users to understand the situation or the feeling of each other more deeply and earlier. A communication system for exchanging the situations and the feelings of both users is provided without performing optional communication operations, such as a telephone call and an e-mail. The condition or the situation on the transmitter side is to be judged and to be notified to the receiver side by inputting bio-information such as breathing, pulse-beats and heartbeats or environment information such as weather, date and hour, ambient temperature, or alternatively, by comparing, synchronizing and/or relating the bio-information and/or the environment information at present with respect to the bio-information and/or the environment information in the past. With respect to the situation of the receiver side, it is also notified similarly to the transmitter side.

8 Claims, 8 Drawing Sheets

U.S. PATENT DOCUMENTS

| | | |
|---|---|---|
| 4,974,607 A | 12/1990 | Miwa |
| 5,437,278 A | 8/1995 | Wilk |
| 6,704,595 B2 * | 3/2004 | Bardy ........................ 600/518 |
| 7,199,708 B2 * | 4/2007 | Terauchi et al. ........ 340/539.12 |
| 2002/0013538 A1 | 1/2002 | Teller |
| 2002/0082486 A1 | 6/2002 | Lavery et al. |
| 2002/0109595 A1 | 8/2002 | Cairo et al. |
| 2003/0001742 A1 | 1/2003 | Eshelman et al. |
| 2003/0009088 A1 | 1/2003 | Korth et al. |
| 2003/0229517 A1 | 12/2003 | Meserol et al. |

FOREIGN PATENT DOCUMENTS

| | | |
|---|---|---|
| DE | 10005526 | 8/2001 |
| GB | 2285135 | 6/1995 |
| JP | 07-234982 | 9/1995 |
| JP | 11-070088 | 3/1999 |
| JP | 11-088518 | 3/1999 |
| JP | 2002-064658 A | 2/2002 |
| JP | 2002-215810 | 8/2002 |
| JP | 2002-344580 A | 11/2002 |
| WO | WO-02/17602 | 2/2002 |
| WO | WO-02/089663 A1 | 11/2002 |
| WO | WO-03/043356 A1 | 5/2003 |

* cited by examiner

Communication process of portable wireless communication terminal on transmitter side Data structure of utilized data

FIG. 5

| Output Device |
|---|
| Speaker |
| Display Device |
| Lighting Device |
| Driving Device |
| .... |

| Environment Information | Measured Value of Environment Information | Bio-Information | Measured Value of bio-Information | Transmission Data |
|---|---|---|---|---|
| Ambient temperature | 10°C or Lower | | | "Cold and cold" |
| Ambient temperature | 11°C to 17°C | | | "Cool and cool" |
| Ambient temperature | 18°C to 25°C | | | "Warm and warm" |
| Ambient temperature | 26°C or Higher | | | "Hot and hot" |
| | | Heartbeats | 60 or Less | "Slow and slow" |
| | | Heartbeats | 61 to 90 | "Pit-a-pat and pit-a-pat" |
| | | Heartbeats | 91 or more | "thumpiy-thump and thumpity-thump" |
| .... | | | | |

Data structure of transmission data by output device

Communication process of portable wireless communication terminal on receiver side Communication process in a case where notification is made in an emergency Process of a case where periodical communications are preformed

COMMUNICATION APPARATUS AND COMMUNICATION METHOD

CROSS-REFERENCE TO RELATED APPLICATIONS

The present application is a continuation of U.S. application Ser. No. 10/863,440, filed on Jun. 8, 2004, now U.S. Pat. No. 7,199,708, the disclosure of which is hereby incorporated by reference herein, and claims priority from Japanese Patent Application No. JP 2003-188421, filed on Jun. 30, 2003.

BACKGROUND OF THE INVENTION

The present invention relates, for example, to a communication system such as a portable communication system, and more particularly relates to a communication apparatus for offering information such as personal information with reference to a transmitter and periphery environment information to a receiver side and further relates to its control method.

In a portable wireless communication terminal, a transmitter appoints a transmission receiver and communicates with a receiver by having a telephone call or by transmitting a message which is created in an e-mail or the like. At that time, the receiver can confirm the telephone number and the like of the transmitter at the time point when an electric wave from the transmitter is received so that the partner can be recognized before a telephone call and the like is actually conducted.

In recent years, it is known a method where a person identification is made by transmitting personal information of a user by means of a portable wireless communication terminal to an objective transmission receiver and the like or a method where bio-information of a user is managed and utilized for a medical treatment at home and the like by transmitting the bio-information of the user to a management center.

With respect to this bio-information managing system using a portable wireless communication terminal, the system is constituted such that a measuring device for measuring the bio-information is connected to the portable wireless communication terminal and bio-information is transmitted to and saved in the management center by means of the portable wireless communication terminal so as to make it possible to transmit a measured result from a management center to a portable wireless communication terminal of a user and to display it therein. Further, a medical staff registered beforehand is to inspect the bio-information saved in the management center and to write in his remarks in the management center such that it is possible to transmit the remarks to the portable wireless communication terminal of the user to be displayed therein and the like.

In Japanese Laid-open Patent No. 2002-215810, there is shown a bio-information management system using a portable wireless communication terminal of a user.

However, these are one way information transmission in which only a telephone number of a transmitter and the like can be confirmed before the reception when receiving an electric wave from a transmitter. Further, even after the reception, there are no means for a receiver to understand the occasional physical condition of a transmitter or an ambient environment other than the information of telephone sounds, characters, videos and the like which a transmitter transmits, and as a result, it cannot be said that a request of a receiver for understanding the actual state of the transmitter more deeply and more early is to be satisfied.

In addition, there was a problem also for a transmitter that he cannot understand the situation of a receiver.

SUMMARY OF THE INVENTION

In view of the aforesaid problem, an object of the present invention lies in that situations and feelings of each other are made to be understood more deeply and more early by offering bio-information of both users and environment information. In addition, it lies in proposing a new communication means for exchanging situations and feelings of each other without conducting optional communicating operations such as telephone calls and e-mails.

According to the present invention, the condition/situation of the transmitter side is judged and notified to the receiver side by inputting bio-information such as breathing, pulse-beats and heartbeats of the transmitter or environment information such as weather, date and hour and ambient temperature, or alternatively by comparing, synchronizing and making a relationship between the bio-information of the transmitter or the environment information at the present time and the past bio-information or environment information. In addition, also with respect to the situation of the receiver side, it is similarly notified to the transmitter side.

In this manner, it becomes possible for both of a transmitter and a receiver to comprehend the situation of the partner side easily by a method other than an actual communication operation. In addition, even in a situation where a telephone call and the like cannot be conducted for the reason of a transmitter or a receiver, it is possible to transmit the situation to the transmitting and receiving partner.

BRIEF DESCRIPTION OF THE DRAWINGS

FIG. 5 is an explanatory diagram showing a data construction example of transmission data by output device according to an exemplified embodiment of the present invention;

DETAILED DESCRIPTION

Hereinafter, one exemplified embodiment of the present invention will be explained with reference to FIG. 1 to FIG. 8. It should be noted in the example of the present invention that information showing heartbeats, pulse-beats, breathing, blood pressure, SpO2 (Blood Oxygen Saturation), electrocardiograms, brain waves, sweating of skin, GSR (Galvanic Skin Response), body movement, MEG (Magnetoencephalography), EMG (Electro-Myography), body surface temperature, diameter size of a pupil, micro-vibration, biochemical reaction and the like will be designated as bio-information. Also, natural information such as date and hour, lunar age, ambient temperature, humidity, weather, atmospheric pressure and the ebb and flow of tide and environment information such as ambient noise, room temperature and a smell will be designated as circumference environment information.

Figure 1:
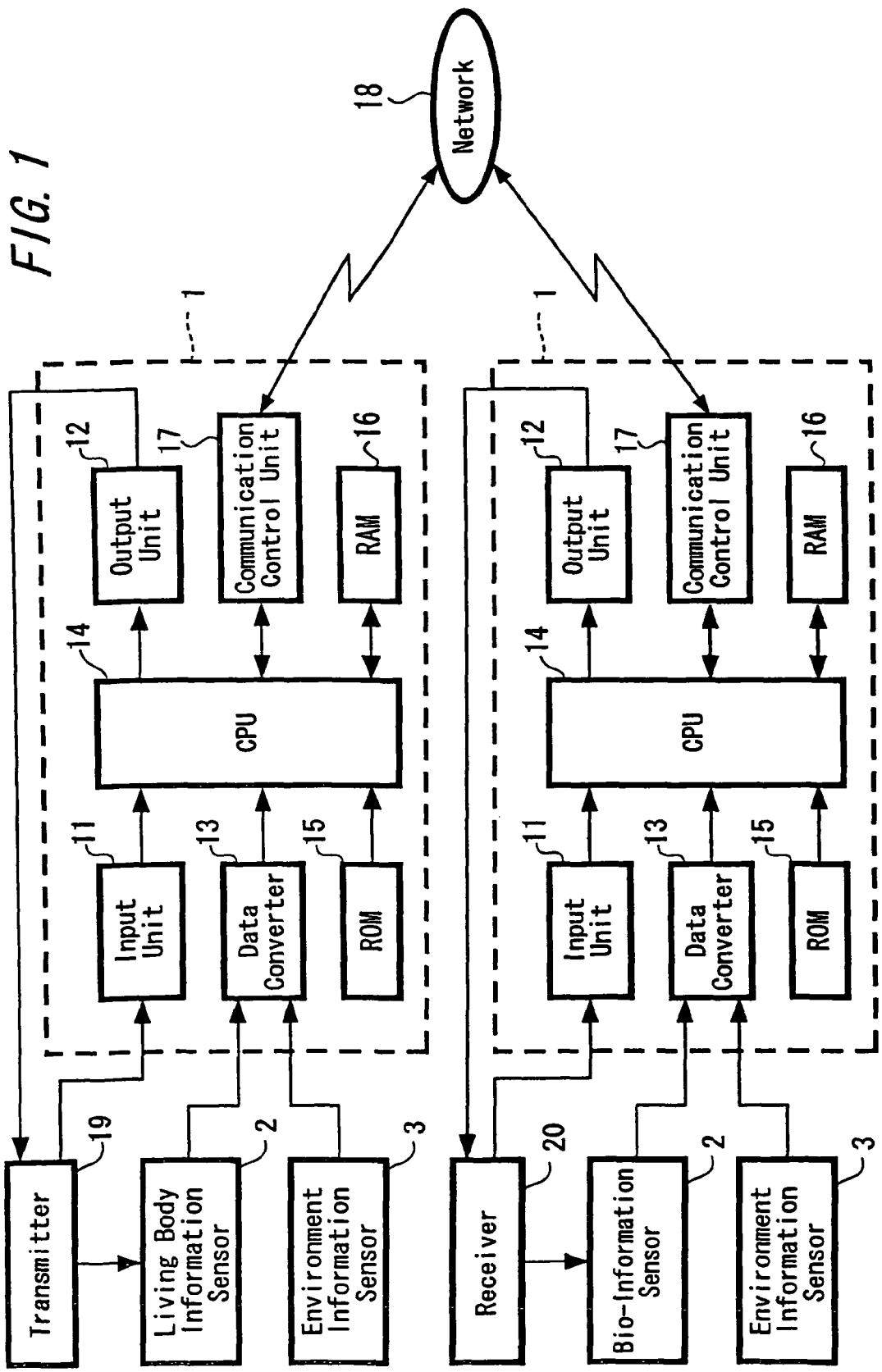
FIG. 1 is a block diagram showing a constitution of a wireless communication apparatus using a portable wireless communication terminal according to one exemplified embodiment of the present invention.

FIG. 1 is a block diagram showing a rough outline of an apparatus constitution according to an example of the present invention. In this example, an explanation will be done with reference to FIG. 1 by taking an example where a portable wireless communication terminal is used as a communication apparatus. This apparatus is composed of a portable wireless communication terminal 1, a bio-information sensor 2 for measuring bio-information of a user and for inputting the information to the portable wireless communication terminal 1 and environment information sensor 3 for measuring ambient environment information and for inputting the information to the portable wireless communication terminal 1.C The portable wireless communication terminal 1 is composed of an input unit 11 to which a user inputs information, an output unit 12 for outputting information, a data converter 13 for converting input information from a bio-information sensor 2 and an environment information sensor 3 from analog to digital, a CPU (Central Processing Unit) 14 executing processes according to information inputted from the data converter 13, a ROM (Read Only Memory) 15, a RAM (Random Access Memory) 16 and a communication control unit 17 for performing a communication through a network 18 according to results processed by the CPU 14.

Here, the input unit 11 includes, for example, buttons and a keyboard for inputting character information, a microphone (sound collecting device) for inputting sounds, a camera (imager device, picture taking device) for inputting pictures or videos, and the like. The output unit 12 includes, for example, a display (display device) for displaying characters, pictures and videos, a speaker for outputting sounds, a lighting device (LCD picture screen, LED or the like) for lighting various kinds of lights, a driving device for shaking the main body, and the like. Also, there are recorded in the ROM 15 with respect to data to be used for programs which describe processing contents of this invention and for processing thereof and the like. Further, there are recorded in the RAM 16 with respect to environment information and bio-information which are contents utilized in the past, setting contents of a user and the like.

The bio-information sensor 2 is a device for measuring bio-information and is, for example, a heartbeat gauge, a blood pressure gauge, a brain wave measuring device and the like. There are types for these sensors such as a type to be mounted onto a portion of a user's body for measuring bio-information thereof and for transmitting the measured result to the portable wireless communication terminal 1 and a type to be installed onto the main body of the portable wireless communication terminal 1 for measuring bio-information of a user when the portable wireless communication terminal is held by a body portion of the user such as his hand and the like.

Figure 2:
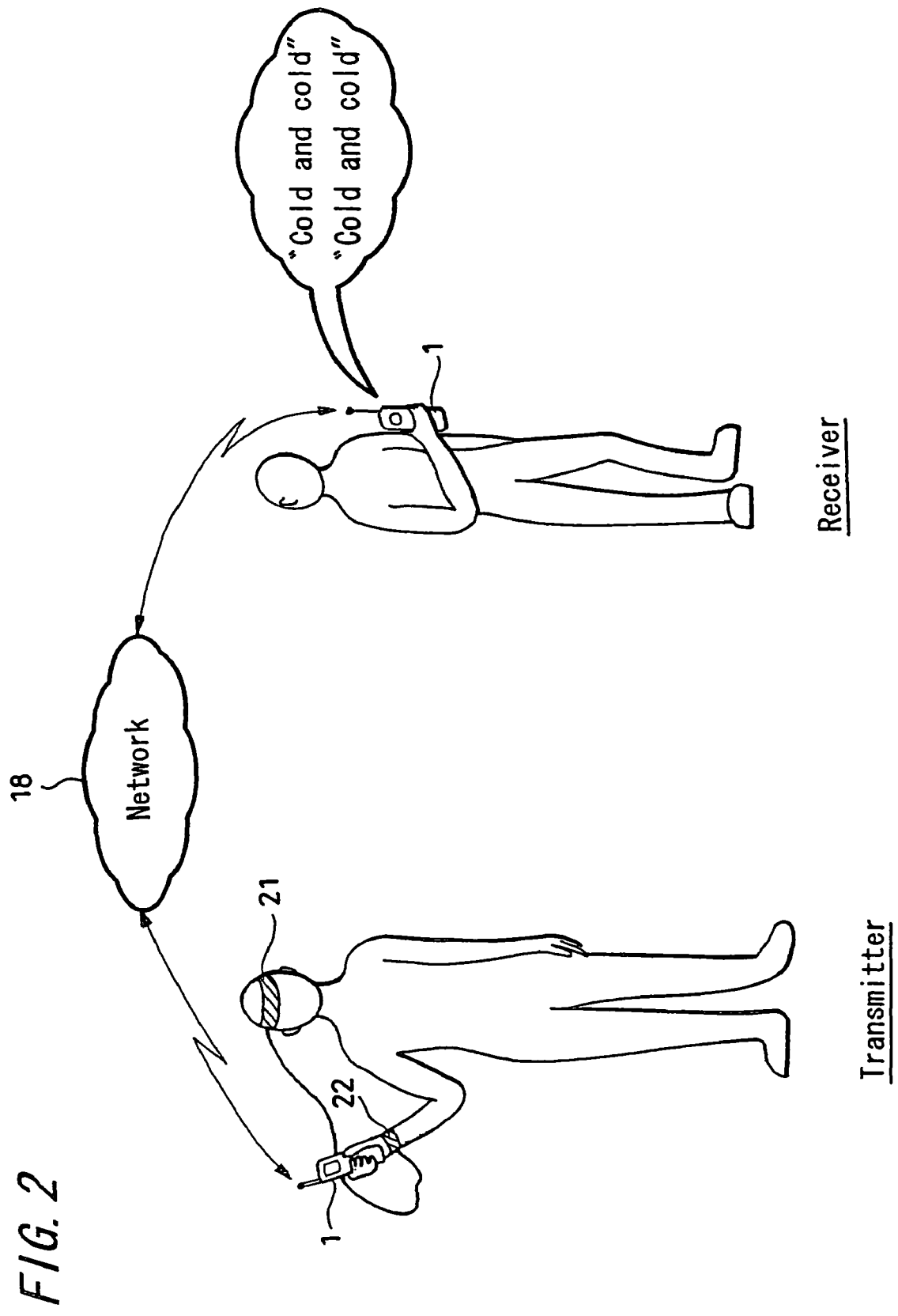
FIG. 2 is a schematic view showing a measure method of bio-information according to one exemplified embodiment of the present invention.

FIG. 2 shows one example of a case where bio-information of a user is measured by the bio-information sensor 2. A brain wave measuring device 21, for example, is constituted by installing electrodes onto a head band and measures brain waves by mounting it on a head portion of a user where it is connected to the portable wireless communication terminal 1 by means of a signal line connected to the head band and the measured result can be transmitted thereto. Also, a blood pressure measuring device 22 is constituted by installing a blood pressure gauge onto a wrist band and measures blood pressure by mounting it on a wrist of a user where the measured result is transmitted to the portable wireless communication terminal 1 similarly as the brain wave measuring device. With respect to these devices, a method was explained as one example where they are mounted onto respective regions of the body for measuring, but it is possible to mount onto other regions of the body for measuring. Further, with respect to a method for transmitting measured results from respective measuring devices to the portable wireless communication terminal 1, it was explained as a method for connecting a signal line directly, but it is needless to say that a wireless transmission is also possible. In addition, there is also a method where a fever thermometer, a heartbeat measuring device and the like are installed onto the portable wireless communication terminal 1 and body temperature and heartbeats are measured when a user grips the terminal by his hand.

An environment information sensor 3 is a device for measuring environment information and is, for example, a clock device, a temperature gauge, a barometer and the like. There are methods for measuring environment information such as a method where measurement is performed by installing these sensors onto the portable wireless communication terminal 1 and a method in a case when it is used indoors or in a vehicle under movement where the results measured by environment information sensors which are installed in the indoor or in the vehicle are transmitted to the portable wireless communication terminal by means of a signal line, wireless and the like.

Figure 3:
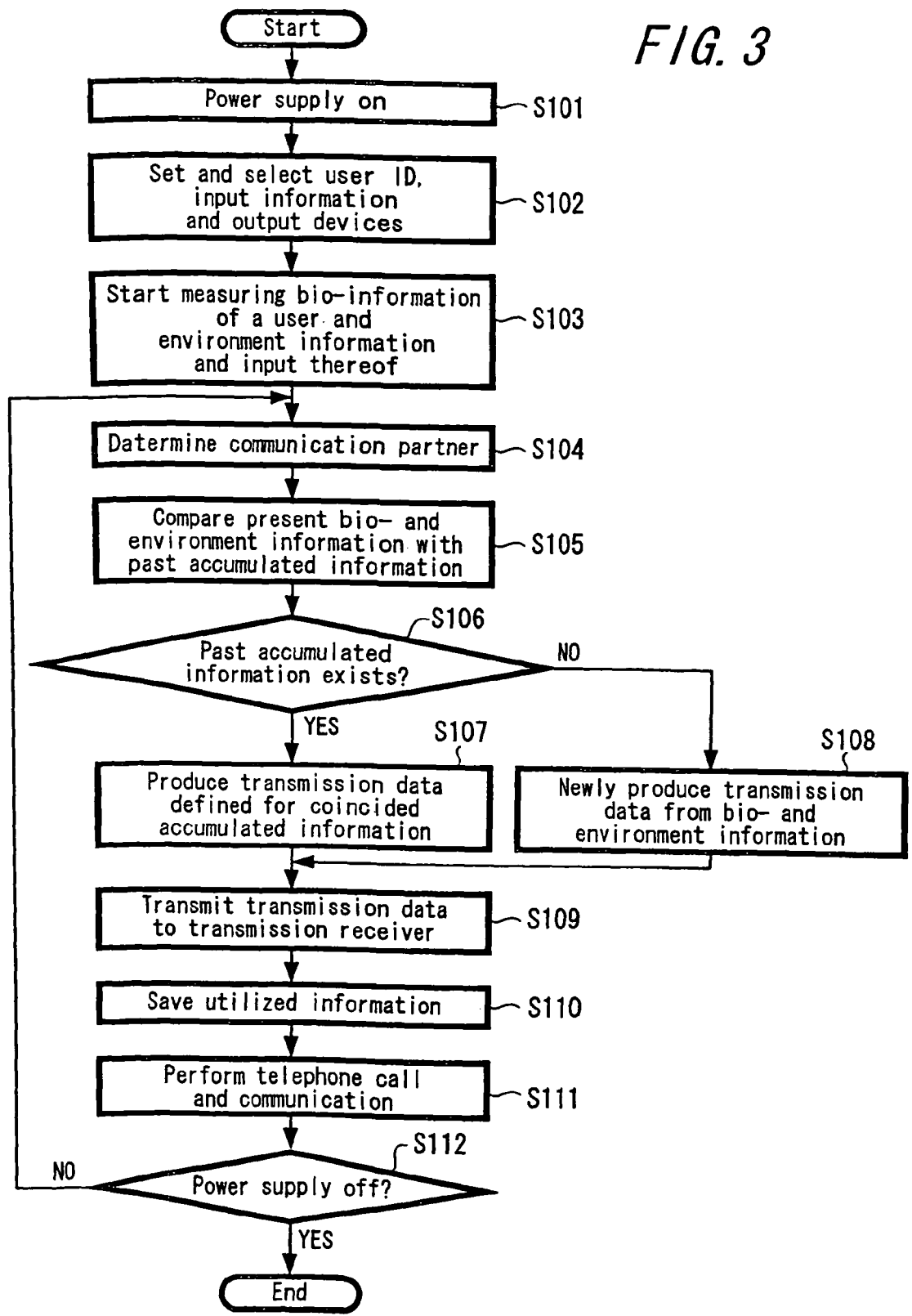
FIG. 3 is a flowchart showing a transmission process according to an exemplified embodiment of the present invention.

A specific first process example using an apparatus explained in the above will be explained with reference to a flowchart shown in FIG. 3. with reference to a flowchart shown in FIG. 3. The process shown in FIG. 3 is a process performed mainly in the CPU 14 in a case when a transmitter transmits a situation on the side of the transmitter to a receiver using the present apparatus by telephone.

First, a power supply of the apparatus is switched on by a user (step S101) and a process starts. A desirable utilized content is inputted by a user from the input unit 1 (step S102). Inputted items are such as a user ID for identifying a user, bio-information and environment information to be measured and used, output devices which a user desires, their setting contents and the like. It should be noted that it is possible to proceed to a subsequent step S103 by skipping this step S102 in a case when these utilized contents were already set beforehand and they are to be utilized directly.

Next, CPU 14 instructs the bio-information sensor 2 and the environment information sensor 3 about the measuring start of the bio-information of a user and the environment information and the measuring is made to start. Then, measured results are inputted from the bio-information sensor 2 and the environment information sensor 3 to the CPU 7 through the data converter 13 (step S103). At that time, it is desirable to apply averaging processing of the bio-information and the environment information along a certain period in the data converter 13 or the CPU 14. The above is an initial setting before a telephone call, an e-mail or the like is initiated.

Next, with respect to a process in case of performing a communication such as a telephone call and an e-mail actually, it will be explained about a case of having a telephone call as an example. First, a transmitter determines a telephone call partner and inputs a telephone number and the like from the input unit 11 (step S104). Then, the CPU 14 compares bio-information and environment information at present with the bio-information and the environment information recorded in the past utilized data which are accumulated in the RAM 16 and searches whether or not there is a history of a telephone call which was performed in a similar condition in the past (step S105). It is judged according to the result whether or not there are similar utilized data in the past accumulated information (step S106), and in a case when similar utilized data exist, transmission data are produced based on the contents recorded in the utilized data (step S107). In a case when it is judged in step S106 that similar utilized data do not exist, transmission data are newly produce based on the bio-information and the environment information at present (step S108).

Figure 4:
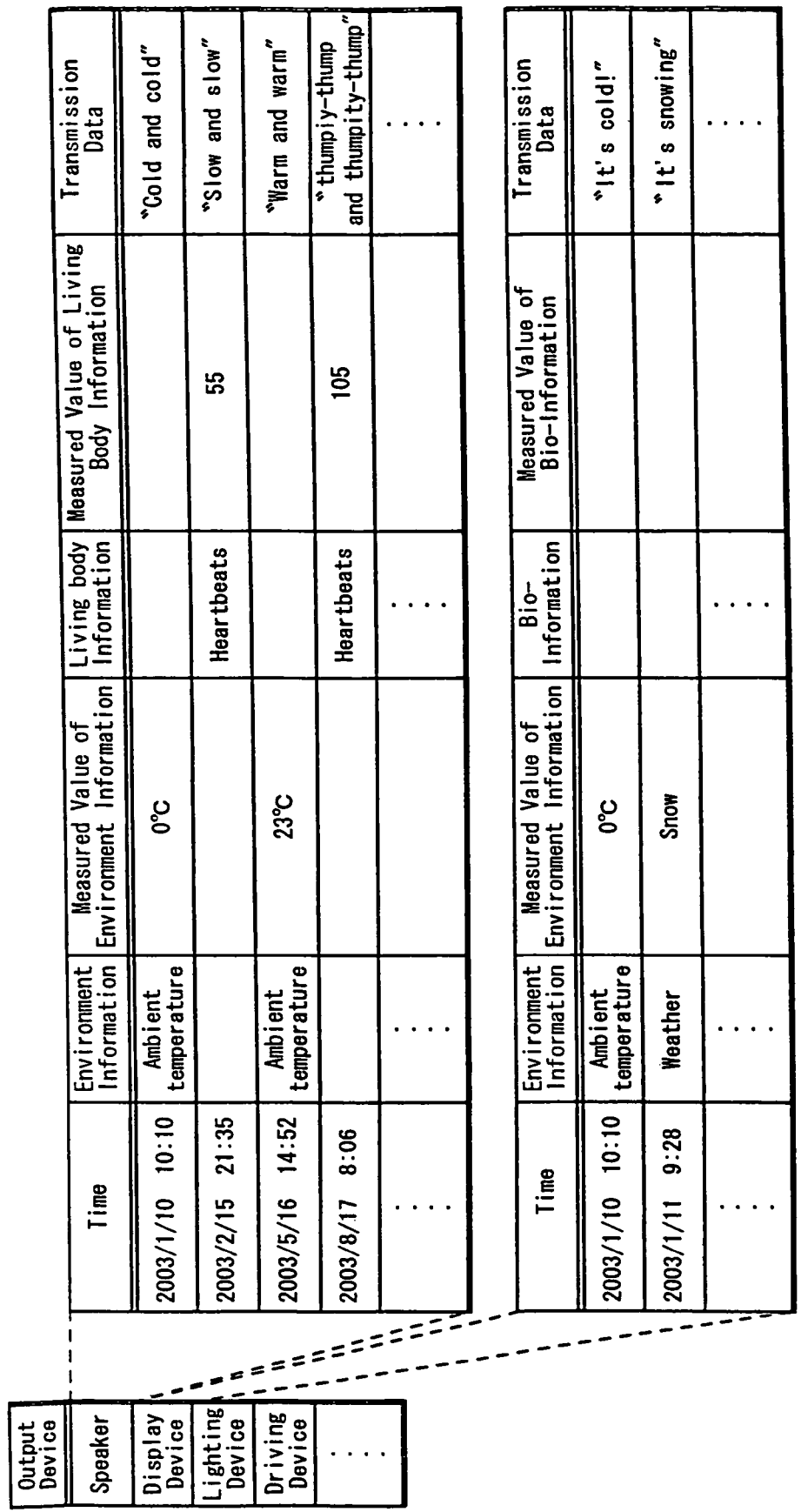
FIG. 4 is an explanatory diagram showing a data construction example of utilized data according to an exemplified embodiment of the present invention.

With respect to a method for producing transmission data based on the past utilized data, it will be explained with reference to FIG. 4. FIG. 4 is one example of a data construction indicating the past utilized data. It will be explained with respect to a case where, for example, ambient temperature is selected as environment information and a speaker is selected as an output device. In a case when, for example, the ambient temperature at present is 0° C., an item is searched in the past utilized data accumulated in the RAM 16 where the measured value of the environment information is 0° C. with respect the ambient temperature. It is supposed as the result that there are 2 affairs of records for having telephone calls at 10 past 10 on Jan. 10, 2003 in a condition of an ambient temperature 0° C. and supposed that contents are recorded as transmission data at that time such that sounds of "cold and cold" are outputted with respect to a speaker of an output device for the first affair and characters of "cold!" are outputted with respect to a display device of an output device for the second affair. According to the present example, since a speaker is selected as an output device, the data of the first affair are employed as the transmission data and transmission data for outputting sounds of "cold and cold" from the speaker are produced.

It should be noted in step S105 that the comparison of the bio-information and environment information at present with the past bio-information and environment information was performed such that it was judged whether or not there are records which coincide with each other in the example mentioned above, but it is possible to judge it by providing a predetermined amount of a permissible range with respect to each information. For example, in a case when the present ambient temperature is 0° C., it will be judged that records included in a range of ±1° C. of the past ambient temperature coincide therewith. According to the aforementioned practical example, ambient temperature was used as a searching key for the environment information, but it is needless to say that bio-information can be further added thereto so as to select transmission data which coincide therewith. Further, it is also possible to add a telephone call partner (transmission receiver) to the items of utilized data so as to select transmission data in response to environment information, bio-information and a transmission receiver.

Next, it will be explained relating to a method for newly producing transmission data with reference to FIG. 5. FIG. 5 is one example of a data construction defining transmission data by output device. Similarly as mentioned above, it will be explained with respect to a case where ambient temperature is selected as environment information and a speaker is selected as an output device. In a case when utilized data for the ambient temperature 0° C. do not exist in the past utilized data accumulated in the RAM 16, the CPU 14 produces transmission data of ambient temperature 0° C. newly based on the database saved in the ROM 15 or the RAM 16. For example, it is supposed that a database as shown in FIG. 5 is saved in the ROM 15 or the RAM 16. Here, the CPU 14 searches data relating to a speaker as an output device and ambient temperature as environment information. As a result, an item in which the contents of the measured values of the environment information are "10° C. or lower" are detected for data corresponding to the ambient temperature 0° C. at present and the definition of the transmission data "cold and cold" for that item is produced as transmission data.

In this manner, transmission data are produced and thereafter the transmission data are transmitted to a transmission receiver by means of the communication control unit 17 (step S109). The CPU 14 saves the transmission data in the RAM 16 together with the bio-information and the environment information at that time (step S110). Thereafter, a transmission partner will have a telephone communication by receiving a telephone call (step S111). Finally, it is judged whether or not the shut-off of the power supply is instructed by the transmitter (step S112) and the process will end at the time point when the shut-off of the power supply is instructed by switching off the power supply, and in case of not the shut-off of the power supply, the measurement of the bio-information of a user and the environment information is performed until a next telephone call.

Figure 6:
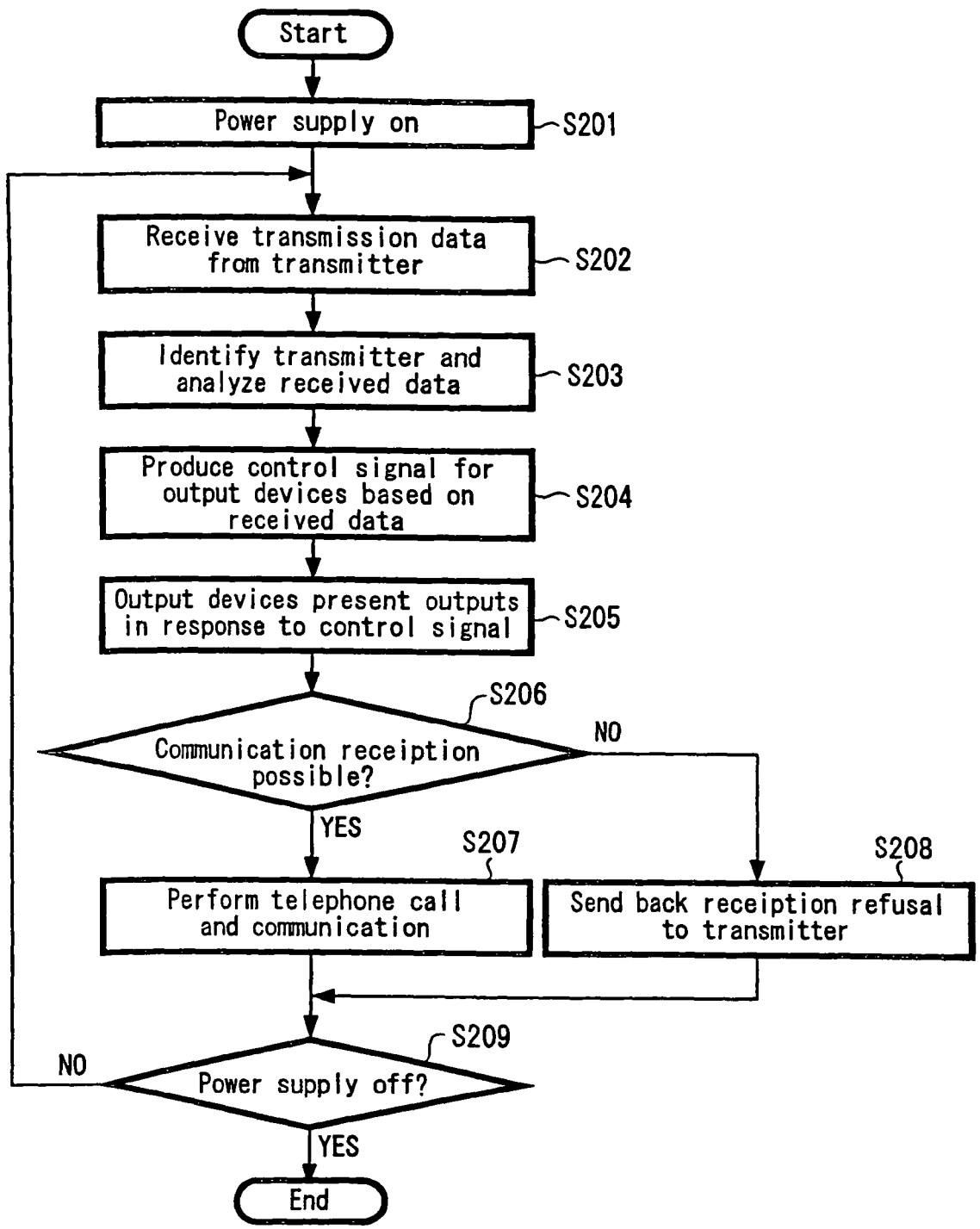
FIG. 6 is a flowchart showing a receiving process according to an exemplified embodiment of the present invention.

As explained above, a process is performed in the portable wireless communication terminal of the transmitter side such that a situation of the transmitter at the time of a telephone call is transmitted to the transmission partner place. On the other hand, an embodiment of a process on the receiving side relating to the first process example will be explained with reference to a flowchart shown in FIG. 6. The process shown in FIG. 6 is a process performed mainly in the CPU 14 in a case when a receiver receives a telephone call from a transmitter by using the present apparatus.

First, the power supply is switched on for the apparatus according to the present example by a user (step S201) and the process starts. When transmission data from the transmitter are received by the Communication control unit 17 (step S202), the CPU 14 identifies the transmitter from the received data and analyzes the received data (step S203). When the transmitter is identified, it is possible to display icon and the like on the display device of the output unit 12 corresponding to the name of the transmitter and the transmitter. With respect to the receiving data, contents relating to data which are outputted to output devices and their output devices are defined and in this example, the information transmitted from the transmitter is assumed to be contents for outputting sounds like "cold and cold" with respect to a speaker of the output device. Therefore, the CPU 14 produces a control signal with respect to the speaker of the output device according to the received data so as to generate a reception sound of a voice like "cold and cold" (step S204). Receiving that control signal, the speaker of the output unit 12 generates the reception sound (step S205).

It is possible for the receiver to understand that the transmitter has a telephone call from a cold place, because the reception sound is generated from the speaker. The receiver judges at that time point whether or not a telephone communication will be possible (step S206) and as a result if a telephone communication is possible, he receives the telephone call by pushing down a reception button and the like so as to execute the telephone communication (step S207), and if it is a case of a situation that a telephone communication cannot be accepted, he will refuse the reception of the telephone call by pushing down a button and the like for sending a reply to the transmitter that the telephone communication cannot be executed (step S208). Finally, it is judged whether or not the shut-off of the power supply is instructed by the receiver (step S209) and the process will end at the time point when the shut-off of the power supply is instructed by switching off the power supply, and in case of not the shut-off of the power supply, a next telephone call will be waited for.

By processing in this manner, it is possible to understand the physical condition and the ambient environment situation before an actual telephone communication with the transmitter when the receiver receives a telephone call and the like.

Further, also with respect to the receiver side, it becomes possible in case of using the present apparatus to transmit the situation of the receiver side to the apparatus of the transmitter side according to the bio-information and the environment information at the time point when the receiver receives a telephone call. By performing in this manner, in a case of a situation when, for example, a receiver cannot have a telephone communication, because he is running in the direction of a destination for an urgent affair, if his heartbeats reaches 100 or more, it becomes possible to transmit transmission data corresponding to heartbeats of 100 or more simultaneously when a refusal of a telephone call reception is sent as a reply to the transmitter. Consequently, it becomes possible for a transmitter not only to recognize the information of the telephone call refusal but also to guess the reason thereof to a certain degree so that it is possible to understand the situation of the partner more deeply and better communication is realized compared with a case where a telephone call is simply refused.

Figure 7:
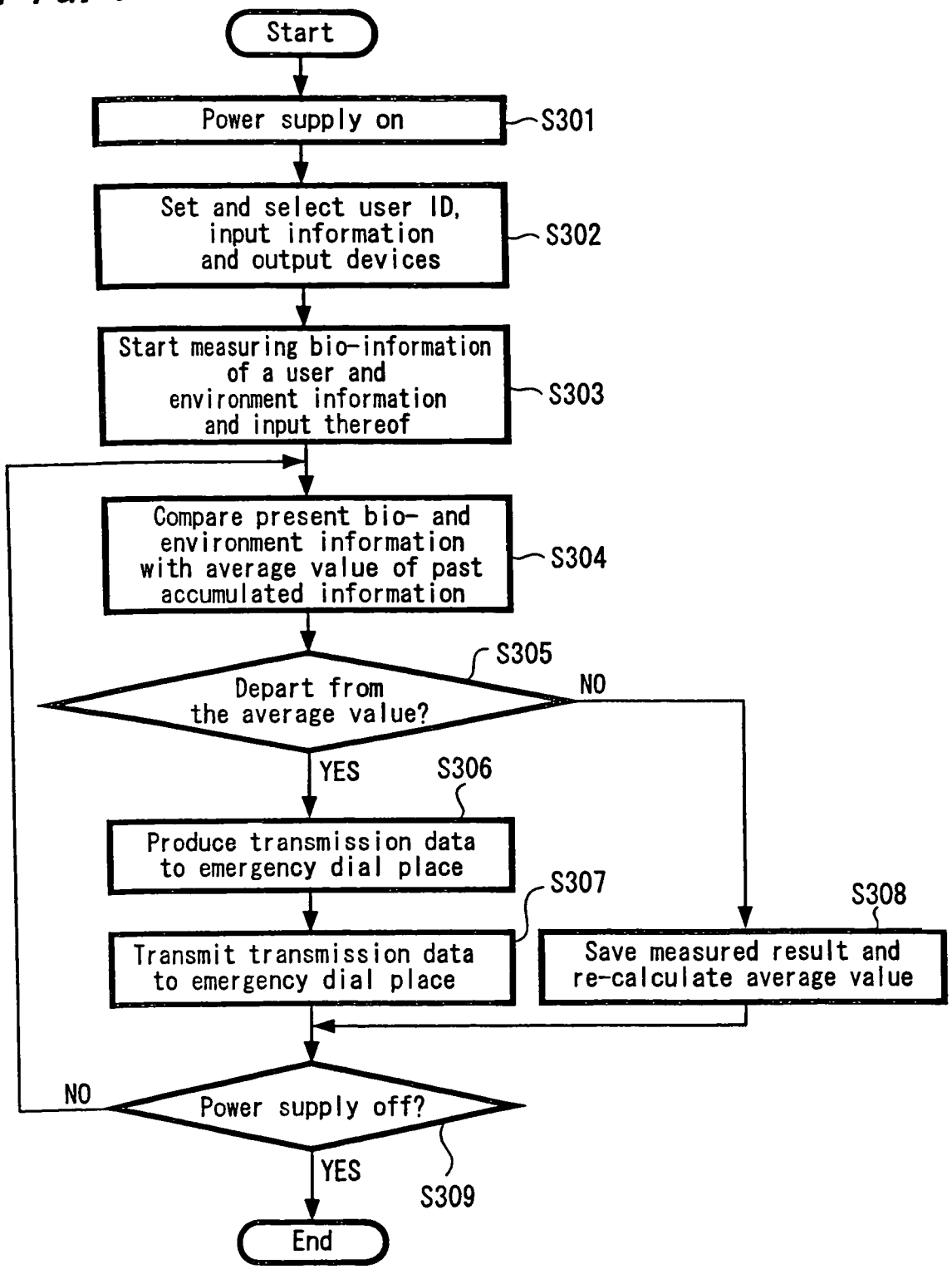
FIG. 7 is a flowchart showing a transmission process according to another exemplified embodiment of the present invention.

As a second process example using the present apparatus, it will be explained with respect to a process of a case where a notification is made in an emergency with reference to a flowchart shown in FIG. 7. The process shown in FIG. 7 is a process performed mainly in the CPU 14 in a case when an emergent notification is sent to a predetermined notifying place when an emergent situation occurs.

Here, from the switching on of the power supply to the measuring start shown as step S301 to step S303 are just similar as the step S101 to the step S103 of FIG. 3 explained previously. However, according to this example, it will be explained with respect to a case where ambient temperature and illumination (brightness) are selected as environment information and heartbeats are selected as bio-information. When the power supply is switched on for the present apparatus and an initial setting is performed, measuring by the bio-information sensor 2 and the environment information sensor 3 will be made to start. During a period when a communication such as a telephone call and an e-mail is not performed, selected information is measured periodically by time and compared with the average value of the past measured information which is accumulated in the RAM 16 (step S304). It is judged whether or not there is a departure of a predetermined amount or more from the average value according to the compared result (step S305) and in a case when there is a departure, it is judged that an emergent situation occurred and transmission data are produced in tune with its content to be transmitted to an emergency dial place (step S306) After the transmission data are produced, the transmission data are transmitted automatically to an emergency dial place which was set up beforehand (step S307). In a case when it is judged that there is no departure by a result of a judgment in step S305, the measured bio-information and environment information will be saved in the RAM 16 and the average value will be re-calculated (step S308). Finally, it is judged whether or not the shut-off of the power supply can be performed and the process will end when the shut-off of the power supply is instructed, and in case of no instruction, the measurement of the bio-information and the environment information will be continued.

It will be explained specifically according to this example with respect to a judging method whether or not an emergent situation occurred. After the process starts, the CPU 14 measures the bio-information and the environment information in a constant cycle and saves the measured result in the RAM 16 in step S308 excluding an emergent period. The average value of the measured values by time is calculated according to the saved information and this is made to be a value of a normal time. In a case, for example, where a user is running with short steps in the direction of a station for going to work in the morning, the average values of data at the start of office hours can be normally supposed such that the ambient temperature is 18° C., the illumination is 50,000-1× and the heartbeats are 95 beats/minute. In addition, in a case where he goes home on foot when going home, the average values of data at the going-home time can be supposed such that the ambient temperature is 17° C., the illumination is 3-1× and the heartbeats are 70 beats/minute. In this case, as a judging method for judging that an emergent situation occurred, it is assumed that it is defined to judge as abnormal at the going-home time in a case when the ambient temperature is within ±5° C. of the value at the normal time, the illumination is additively within ±5-1× of the value at the normal time and the heartbeats are increased further by 20 or more. At this time, in a case where the data at the going-home time on a certain day are measured such that the ambient temperature is 15° C., the illumination is 0.5-1× and the heartbeats are 110, it can be assumed that the heartbeats became abnormal in a dark place outdoors so that it is judged that there exist some kind or another dangerous condition and it is notified to the emergency dial place.

However, in a case when data of a certain day are measured in the same condition such that the ambient temperature is 23 degrees, the illumination is 250-1× and the heartbeats are 92 beats/minute, it is not made as an object of an emergent notification, because the possibility that it is in a certain place having an indoor illumination is high. However, it is assumed that an action different from that of a normal time is taken in such a case so that if the data are to be included in the calculation for calculating the normal condition, the reliability of the normal time value will be lowered. Therefore, it is possible to take a process for not performing a re-calculation of the average value in a case when the measured result was apart from the average value by a fixed value or more.

Also, the example of the judgment method for the aforementioned emergent situation occurrence was related to a case of a going-home time, but it is possible to detect dangers at various stages by similarly defining judgment methods relating to time zones of going to work and others.

The definitions for judging the emergent situation occurrences used according to the present example are stored in the ROM 15 beforehand, but it is possible to constitute such that they are stored in the RAM 16 and to update them through the network or an external memory medium when it is necessary.

By processing in this manner, it becomes possible to notify dangers promptly by judging the situation and notifying it automatically according to the present apparatus in a case when emergency situations such as an encounter with a dangerous situation occur even if the user is in a situation that he cannot notify by himself.

It should be noted that according to the present embodied examples, the average value of the accumulated past information was made to be calculated in order to obtain bio-information and environment information at a normal time, but it is possible to apply predetermined operations further depending on the kind of information. For example, it becomes easier for the data such as illumination to be made to correspond to the human sense if a logarithmic operation is applied thereto and it can be assumed that a logarithmic operation is to be applied before the process of averaging.

Figure 8:
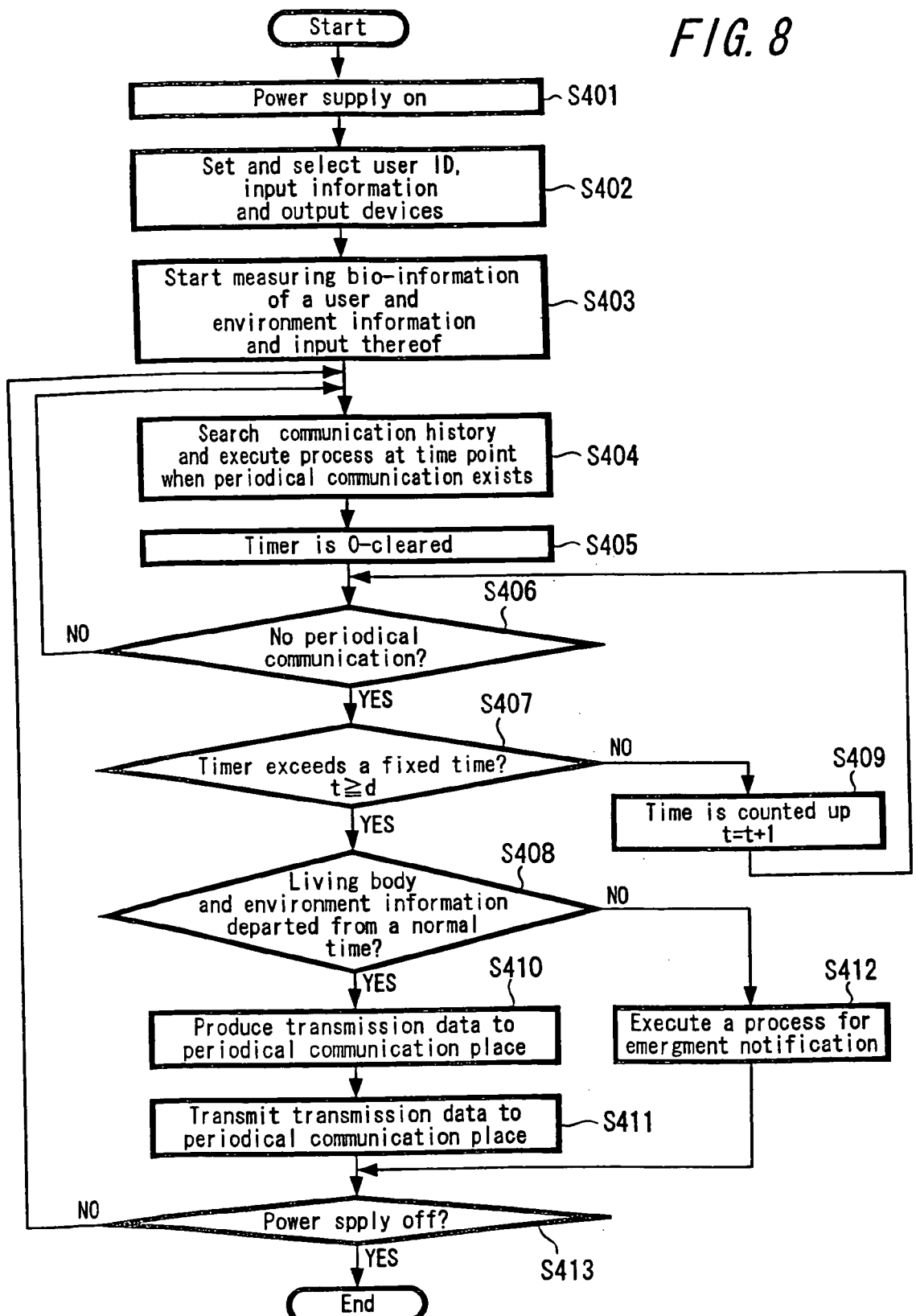
FIG. 8 is a flowchart showing a transmission process according to still another exemplified embodiment of the present invention.

Next, as a third process example using the present apparatus, it will be explained with respect to a process of a case where periodical communications are performed automatically with reference to a flowchart shown in FIG. 8. The process shown in FIG. 8 is a process performed mainly in the CPU 14 in a case when a user performs periodical communications to a specific transmission partner periodically by telephone, e-mail transmission and the like and a situation that a communication cannot be performed by some kind or another reason occurs such that a communication to the transmission partner is performed automatically.

Here, from the switching on of the power supply to the measuring start shown as step S401 to step S403 are just similar as the step S101 to the step S103 of FIG. 3 explained previously. According to this example, in a case when communications such as telephone calls and e-mails are performed, it is assumed that those of the history will be stored in the RAM 16. First, the CPU 14 searches the communication history in the RAM 16 and makes a search whether or not a periodical communication exists. The periodical communication is judged by a fact that a communication is performed to a specific transmission receiver at a certain specific time zone. For example, it is such a case that a telephone call to home is performed at approximately 18 o'clock everyday. As a result, in a case when a periodical communication exists, the present process starts at a time point when it becomes that time (step S404). First, a timer is 0-cleared (step S405). Next, it is judged whether or not a periodical communication was performed (step S406) and in a case when a periodical communication existed, a process for a next periodical communication is performed. In a case when a periodical communication does not exist, it is judged whether or not the timer exceeds a fixed time (d) (step S407) and in a case when it does not exceed it, the timer is counted up (step S409) so as to judge once again repeatedly whether or not a periodical communication exists. In a case when a periodical communication is not performed even if the timer exceeds the fixed time, it is judged that a user did not perform a periodical communication and a process for performing a periodical communication is taken automatically.

In a case if a periodical communication was not performed, first, measured values of bio-information and environment information are compared with the values at a normal time and it is judged whether or not there is an abnormal situation (step S408). If there is an abnormal situation, it is judged that an emergent situation occurred and a notification is transmitted to an emergency dial place (step S412). If there is no abnormal situation, transmission data to the periodical communication place are produced (step S410) and that content is transmitted to the periodical communication place (step S411). In a case if, for example, any abnormal situation cannot be especially seen in the bio-information and the environment information when a user who has a telephone communication to his home at approximately 18 o'clock everyday does not have a telephone call for a certain fixed period, for example, for 30 minutes or more after 18 o'clock, the present apparatus produces transmission data such as a content of "I will communicate later on, because I cannot go home yet." and transmits that automatically to his home.

With respect to the contents of the transmission data in a case when a periodical communication cannot be performed, there are methods such as a method where a user sets as an initial setting in step S403 and a method where it is registered in the ROM 15 or the RAM 16 beforehand such that the contents thereof are to be used. In addition, they can be one kind of a sentence of a fixed format or can be set individually for each kind of the periodical communication.

Further, in the present examples, it was explained with reference to a method for communicating automatically by using the present apparatus in a case when a periodical communication cannot be performed, but it is possible to adopt a process for making a user apprehend that a periodical communication is not performed yet by outputting a notification that a periodical communication was not performed to either one of the output devices in the output unit 12.

By processing in this manner, the present apparatus will perform a communication instead even if it becomes a situation where a communication cannot be performed with respect to the transmission receiver with which communications are performed periodically so that the transmission receiver can confirm that there is no abnormal situation and can feel safe and secure. Also, it might happen that the transmission receiver worries about non-communication and tries to make a communication to the transmitter for a confirmation, but such an activity becomes needless such that useless communications decrease.

As the above, it was explained with respect to exemplified embodiments relating mainly to a portable wireless communication terminal, but it is needless to say that a communication form by means of infrared is applicable and a wire communication form by means of conductive lines such as a public telephone line and internet or by means of an optical fiber and the like is also applicable. Also, it is possible to apply the present constitution and the processes with respect to communication systems other than the portable communication terminal. For example, it can be applied to a fixed telephone and a TV telephone, a video conference, a game and the like. These communication systems are types where communications are performed bilaterally between one to one or one to multiple communication apparatuses and with respect to them, it is possible to realize similar processes by employing similar constitutions as the exemplified embodiments already explained. Further, it is necessary that a user lies in the vicinity of the communication apparatus in a case when these communications are performed, but an occasion might happen where a receiver is missing when a transmitter wants to communicate with him. In such a case, it becomes possible to perform a process for notifying to the transmitter side by judging whether the receiver is at home or away from home based on the bio-information of the receiver and the environment information according to the communication apparatus. In this manner, it does not happen that the transmission partner has a telephone call while the receiver is away from home, waits for the receiver until he appears or the like. Further, it becomes possible to enjoy games on the network by making communications only with favorable partners after the conditions of the communication partners are comprehended beforehand.

According to the present invention, it becomes possible to recognize the physical condition and the ambient environment situation of the communication partner other than information as communication means such as telephone and possible to understand the partner much better.

Also, according to the present invention, it becomes possible to notify dangers promptly by making an emergent notification automatically in a case when an emergency situation occurs where a user encounters with a dangerous condition and the like even in a situation that the user himself cannot communicate by telephone and the like.

Further, according to the present invention, it becomes possible to confirm whether he is safe or not without a communication for confirmation from the periodical communication place by performing a communication automatically to the periodical communication place in a case where a user performed periodical communications but there occurred a situation that that communication was not performed.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

The invention claimed is:

1. A communication apparatus for communicating with a transmission receiver having a plurality of output devices, said apparatus comprising:
    a bio-information sensor for measuring bio-information obtained from a user's body;
    an environment information sensor for measuring environment information of an environment in which the user exists;
    acquisition means configured to acquire at least one of the bio-information and the environment information in accordance with at least one item set by the user;
    means for enabling the user to select an output device from among the plurality of output devices of the transmission receiver;
    storage means for storing acquired information acquired by the acquisition means with respect to the selected output device associated therewith;
    means for determining whether any previously acquired bio-information and environment information for use with the selected output device stored in the storage means exists which is the same as that of presently acquired information, and for causing transmission data to be produced based on the previously acquired information when similar previously acquired information is determined to exist and for causing the transmission data to be produced based on the presently acquired information when the similar previously acquired information is determined not to exist; and
    communication means for transmitting the transmission data to the transmission receiver,
    in which during operation signals representative of at least some of the transmission data are supplied to the output device selected by the user.

2. A control method for controlling communication between a communication apparatus and a transmission receiver having a plurality of output devices, said method comprising:
    detecting at least one piece of information in bio-information of a user of the communication apparatus and in environment information of an environment in which the user exists;
    acquiring at least one of the bio-information and the environment information in accordance with at least one item set by the user;
    enabling the user of the communication apparatus to select an output device from among the plurality of output devices of the transmission receiver;
    storing acquired information with respect to the selected output device associated therewith in a memory device;
    determining whether any previously acquired bio-information and environment information for use with the selected output device stored in the memory device exists which is the same as that of presently acquired information by use of a computer processing device, and causing transmission data to be produced based on the previously acquired information when similar previously acquired information is determined to exist and causing the transmission data to be produced based on the presently acquired information when the similar previously acquired information is determined not to exist; and
    transmitting the transmission data to said transmission receiver,
    in which during operation signals representative of at least some of the transmission data are supplied to the output device selected by the user.

3. The communication apparatus according to claim 1, wherein an operator of the transmission receiver receives the transmission data and may respond to the communication apparatus, whereby the user and the operator can communicate with each other.

4. The communication apparatus according to claim 1, wherein the transmission receiver can transmit bio-information or environment information to the communication apparatus.

5. The control method according to claim 2, wherein an operator of the transmission receiver receives the transmission data and may respond, whereby the user and the operator can communicate with each other.

6. The control method according to claim 2, wherein the transmission receiver can transmit bio-information or environment information.

7. The communication apparatus according to claim 1, in which the plurality of output devices include a display and a speaker.

8. The control method according to claim 2, in which the plurality of output devices include a display and a speaker.

* * * * *